United States Patent
Al Ahmad et al.

(10) Patent No.: US 10,722,124 B2
(45) Date of Patent: Jul. 28, 2020

(54) APPARATUS AND METHOD FOR PHYSIOLOGICAL MECHANICAL AND ELECTRICAL ACTIVITY MONITORING

(71) Applicant: United Arab Emirates University, Al Ain (AE)

(72) Inventors: Mahmoud F. Y. Al Ahmad, Al Ain (AE); Nabil Bastaki, Al Ain (AE); Bisni Fahad Mon, Al Ain (AE)

(73) Assignee: United Arab Emirates University, Al Ain (AE)

( * ) Notice: Subject to any disclaimer, the term of this patent is extended or adjusted under 35 U.S.C. 154(b) by 916 days.

(21) Appl. No.: 15/095,956

(22) Filed: Apr. 11, 2016

(65) Prior Publication Data

US 2017/0127951 A1 May 11, 2017

Related U.S. Application Data

(60) Provisional application No. 62/253,496, filed on Nov. 10, 2015.

(51) Int. Cl.
| | |
|---|---|
| *A61B 5/021* | (2006.01) |
| *A61B 5/029* | (2006.01) |
| *A61B 7/04* | (2006.01) |
| *A61B 5/00* | (2006.01) |
| *A61B 5/0205* | (2006.01) |
| *A61B 5/0245* | (2006.01) |
| *A61B 5/024* | (2006.01) |
| *A61B 5/11* | (2006.01) |

(52) U.S. Cl.
CPC .............. *A61B 5/021* (2013.01); *A61B 5/029* (2013.01); *A61B 5/6823* (2013.01); *A61B 5/7246* (2013.01); *A61B 5/7275* (2013.01); *A61B 7/04* (2013.01); *A61B 5/002* (2013.01); *A61B 5/0205* (2013.01); *A61B 5/0245* (2013.01); *A61B 5/02438* (2013.01); *A61B 5/1102* (2013.01)

(58) Field of Classification Search
None
See application file for complete search history.

(56) References Cited

U.S. PATENT DOCUMENTS

| | | | |
|---|---|---|---|
| 6,535,754 B2 * | 3/2003 | Fishbein | A61B 5/055 600/411 |
| 2008/0154144 A1 * | 6/2008 | Unver | A61B 5/02028 600/528 |
| 2011/0021928 A1 * | 1/2011 | Giovangrandi | A61B 5/0205 600/484 |

OTHER PUBLICATIONS

Al Taradeh, N., et al., "Non-Invasive Piezoelectric Detection of Heartbeat Rate and Blood Pressure." Electronics Letters, Mar. 19, 2015, vol. 51, No. 6, 2 pages.

(Continued)

*Primary Examiner* — Michael R Bloch
(74) *Attorney, Agent, or Firm* — Fitch, Even, Tabin & Flannery LLP

(57) ABSTRACT

The invention describes a method for extracting several physiological parameters such as cardiac cycle parameters with one single measurement over a time period and for monitoring mechanical and electrical cardiac activity. The invention finds its use in providing continuous monitoring of heart mechanical and electrical activities over time. Such signal may be transmitted to clinics of family doctors to keep track of the subject's health.

19 Claims, 3 Drawing Sheets

(56) References Cited

OTHER PUBLICATIONS

Jansen-Park, So-Hyun, et al., "A Monitoring and Physiological Control System for Determining Aortic Valve Closing With a Ventricular Assist Device." European Journal of Cardio-Thoracic Surgery, 2014, vol. 46, pp. 356-360.

Pieraccini, Massimiliano, et al., "Detection of Breathing and Heartbeat Through Snow Using a Microwave Transceiver." IEEE Geoscience and Remote Sensing Letters, Jan. 2008, vol. 5, No. 1, pp. 57-59.

Piskulak, P., et al., Computer Program for Automatic Identification of Artifacts in Impedance Cardiography Signals Recorded During Ambulatory Hemodynamic Monitoring. XIII Mediterranean Conference on Medical and Biological Engineering and Computing, 2013, IFMBE Proceedings, vol. 41, pp. 766-769.

\* cited by examiner

APPARATUS AND METHOD FOR PHYSIOLOGICAL MECHANICAL AND ELECTRICAL ACTIVITY MONITORING

CROSS REFERENCE TO RELATED APPLICATION

This application claims the benefit of Provisional Application No. 62/253,496, filed Nov. 10, 2015, entitled "Apparatus and Method for Cardiac Mechanical Activity Monitoring," which is incorporated herein by reference in its entirety.

TECHNICAL FIELD

This invention relates generally to monitoring of physiological mechanical and electrical activity and more particularly to physiological activity monitoring using piezoelectric material and signal processing techniques.

BACKGROUND

Monitoring of the heart's mechanical and electrical dynamics and its immediate periphery is essential to fully characterise and understand its functionality and variations. The monitoring and early detection of any abnormalities or variations in the cardiac cycle functionality are very critical and have significant impact on the prevention of disease and associated complications. Heartbeat rate and blood pressure are two heart parameters that are fundamental for the prediction of any heart abnormalities.

Attention so far has been focused on assessing the biophysical properties of the heart's components using conventional measurement approaches such as the ECG, blood pressure and heartbeat meters to obtain measurements for such parameters. These traditional techniques are time consuming because of the need for installing multiple probes on the subject to obtain reliable measurements. They also require expensive, bulky and not easily accessible equipment. Furthermore, such equipment allow for the monitoring of the cardiac parameters only when the subject is in proximity to the dedicated equipment.

There is a desire in the field for continuous and real-time monitoring capabilities and the development of techniques to measure a wide range of cardiac cycle parameters effectively, using easily accessible contactless probing systems.

SUMMARY

The invention has several aspects. One aspect provides for a method of monitoring a mechanical and electrical physiological activity of a subject using piezoelectric material coupled to a body part of the subject. The method includes: obtaining a first piezoelectric electrical signal from the piezoelectric material, the first piezoelectric electrical signal is based on mechanical movement of the body part, the mechanical movement related to the physiological activity of the subject. The method also includes manipulating the first piezoelectric electrical signal using signal processing techniques; and extracting from the manipulated first piezoelectric electrical signal at least one first physiological electrical signal related to at least one physiological parameter. The at least one first physiological signal is representative of a physiological feature of the subject.

In one aspect of the invention, the step of manipulating the first piezoelectric electrical signal includes: mapping the first piezoelectric electrical signal to a conventional electrical signal obtained using conventional techniques for the at least one physiological parameter of the subject. The conventional electrical signal is obtained only once and is obtained simultaneously with obtaining the first piezoelectric electrical signal, where the first piezoelectric electrical signal and the conventional electrical signal are obtain for at least one full cycle of activity for the at least one physiological parameter.

In some embodiments, the mapping of the first piezoelectric electric signal to the conventional electrical signal may be performed using a linear one-to-one mapping. In other embodiments, different mapping techniques known in the art may be used.

In a related embodiment of the invention, the signal processing techniques described in the method include generating a transfer function representative of the at least one physiological parameter. The method may further include storing the transfer function on a memory storage device.

The method may further include: obtaining a second piezoelectric electrical signal different from the first piezoelectric electrical signal. The second piezoelectric electrical signal is based on a second mechanical movement of the body part at a time after obtaining the first piezoelectric electrical signal. The second mechanical movement is related to the physiological activity of the subject. The method also includes the step of manipulating the second piezoelectric electrical signal using the signal processing techniques, where the signal processing techniques include convolving the second piezoelectric electrical signal with the transfer function. The method further includes extracting from the second piezoelectric electrical signal at least one second physiological electrical signal related to the at least one physiological parameter, where the at least one second physiological electrical signal represents the same physiological feature of the at least one first physiological signal.

In some embodiments of the invention, the method further includes the steps of: comparing the at least one first physiological electrical signal with the at least one second physiological electrical signal; and assessing if the subject is healthy based on the comparison.

In some embodiments of the invention, obtaining the first piezoelectric electrical signal and the conventional electrical signal is performed when the subject is in good health condition.

In other embodiments of the invention, the physiological activity is cardiac activity. Also, the at least one physiological parameter is a cardiac parameter and obtaining the first piezoelectric electrical signal and the conventional electrical signal is performed when a breath of the subject is held. In some embodiments, where the subject is not human, it is not necessary for the subject to hold its breath in this embodiment.

In some related embodiments of the invention, the at least one cardiac parameter is one of Aortic Pressure AP, Left Ventricle Pressure LVP, Left Atrial Pressure LAP, Left Ventricular Volume LV Vol, and heart sounds.

Some embodiments of the invention described above also include the step of: comparing the at least one first physiological signal and the at least one second physiological signal; and assessing the subject to have a positive condition or a negative condition based on the comparison. In some cases, the subject is assessed to have the positive condition if the at least one second physiological signal is substantially similar to the at least one first physiological signal. In other cases, the subject is assessed to have the negative condition when the at least one second physiological signal is substantially dissimilar from the at least one first physiological signal.

In some related embodiments of the invention, the subject may be notified of the positive or negative conditions. Also, third parties may be notified of the positive or negative conditions. The notification may be provided in different forms and the message of the notification may vary.

In some embodiments of the invention, the step of manipulating the first piezoelectric electrical signal using signal processing techniques includes: wirelessly transmitting the first piezoelectric electrical signal using a transmitter; receiving the transmitted first piezoelectric electrical signal using a receiver located at a location away from the transmitter. In the same embodiment, the step of extracting from the manipulated first piezoelectric electrical signal the at least one first physiological electrical signal related to the at least one physiological parameter is performed at the location of the receiver. Therefore, such embodiment allows for remote monitoring of the subject's physiological activity. Also, by transmitting the first piezoelectric electrical signal away from the subject's body, near which the transmitter is located, this allows for the measurement to be conducted with ease and at any location, where it may be difficult to use conventional measuring techniques.

Some related embodiments of the invention may also include the steps of: comparing the first piezoelectric electrical signal to a pre-determined threshold before transmitting it by the transmitter and amplifying the first piezoelectric electrical signal before transmitting it if the first piezoelectric electrical signal is determined to be below a pre-determined threshold. The method also includes the step of comparing the first piezoelectric electrical signal after receiving it by the receiver and amplifying the first piezoelectric electrical signal after receiving it by the receiver if the first piezoelectric electrical signal is determined to be below the pre-determined threshold.

In some embodiments of the invention, the method may involve the step of storing in the memory storage device a plurality of conventional electrical signals obtained from the conventional measuring techniques, where each of the plurality of the conventional electrical signals correspond to a known separate physiological defect of the at least one physiological parameter; and where the plurality of conventional electrical signals form a pull-up library. The plurality of conventional electrical signals may be for subjects of different physiological and physical characteristics. In the same embodiment, the at least one first physiological electrical signal is compared to each of the plurality of conventional electrical signals and the subject is assessed to have a physiological defect of the at least one physiological parameter based on the comparison, where the defect is determined to be present if the at least one first physiological electrical signal is substantially similar to one of the plurality of conventional electrical signal at certain marker positions of the signal.

In another aspect of the invention, the physiological activity is periodic and the monitoring of the physiological activating is performed continuously. The method further includes: obtaining additional piezoelectric electrical signals different from the first piezoelectric electrical signal. The additional piezoelectric electrical signals are obtained individually and sequentially after the first piezoelectric electrical signal and the additional piezoelectric electrical signals are based on additional mechanical movement of the body part related to the physiological activity of the subject. The method would also include the step of manipulating each of the additional piezoelectric electrical signals using the signal processing techniques, which may include convolving each of the additional piezoelectric electrical signals with the transfer function. Once convolved with the transfer function, at least one additional physiological electrical signal related to the at least one physiological parameter is extracted from each of the additional piezoelectric electrical signals. The method may further include the step of comparing the at least one first physiological electrical signal and its corresponding features and the at least one additional physiological electrical signal and its corresponding feature for each of the additional piezoelectric electrical signals and determining the health status of the subject based on the comparison. Because of the periodic nature of the signal, the method may provide for continuously assessing if the subject is healthy based on the comparison.

The results, as provided above, may be communicated to the user or the subjection or it may be communication to a third party such as physicians, hospital, family members or the like.

BRIEF DESCRIPTION OF THE DRAWINGS

The accompanying drawings illustrate non-limiting example embodiments of the invention.

DETAILED DESCRIPTION

Throughout the following description specific details are set forth in order to provide a more thorough understanding to persons skilled in the art. However, well known elements may not have been shown or described in detail to avoid unnecessarily obscuring the disclosure. The following description of examples of the technology is not intended to be exhaustive or to limit the system to the precise forms of any example embodiment. Accordingly, the description and drawings are to be regarded in an illustrative, rather than a restrictive, sense.

The modelling of cardiac time domain impulsive response for any living organism that has a beating heart or organ, where such response contains the fine features as well as pronounce the chest functionality is not yet developed. This invention presents a method and apparatus which combines both piezoelectric and signal processing techniques to estimate such cardiac response. More specifically, a method and apparatus are described to electrically model the cardiac corresponding mechanical activities in time domain.

Piezoelectric based transducers technology could convert one form of energy into another. They have a range of uses, particularly as sensors. The piezoelectric effect has been used in thousands of sensing applications. These applications range from infrared sensors, stress gauges, and vibration detectors. The use of piezoelectric component can be quite advantageous, since the piezoelectric components would need fewer parts to fulfill the desired functionality.

Mechanical movement on the surface of a body of a living organism that has a beating heart of organ is caused, at least in part, by mechanical movement of the internal organs such as the contractions and expansions of the heart muscles. The current disclosure may refer hereinafter to the activity of a heart in a human or a person or a subject; however, it is to be understood that the teachings in this disclosure covers activity of any moving organ in any living organism.

When piezoelectric material is attached to the person's body, such movement models a mechanical load and produces a relative induced strain on the piezoelectric material, which in turn causes the piezoelectric material to generate a corresponding conformal voltage signal. This voltage signal may be mapped with the heart's actions and the resultant voltage signal may be used to extract and model the corresponding heart parameters using piezoelectric and signal processing theories. Furthermore, explicit expressions may be derived that relate the voltage output signal describing the heart pressures and other relative parameters based on the electromechanical coupling analogy. Different mapping techniques known in the art may be used. By way of non-limiting example, a linear one-to-one mapping may be used.

Figure 1:
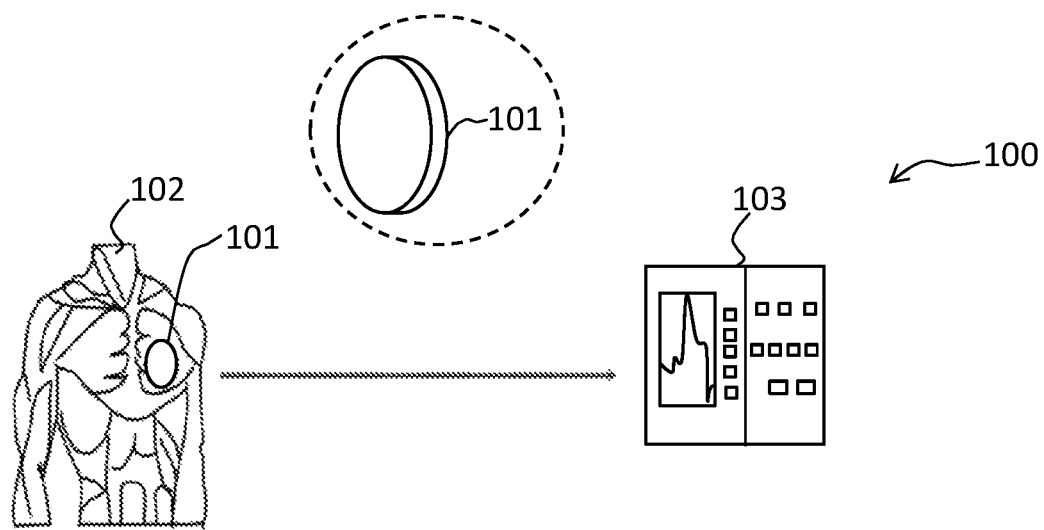
FIG. 1 shows a schematic representation of a cardiac monitory system according to an example embodiment.

FIG. 1 shows a schematic representation of a cardiac monitory system 100 in an embodiment of the invention. System 100 shows piezoelectric sensor 1 is placed on the anterior chest surface of a person 2. The piezoelectric sensor 1 used in this embodiment is a sheet sensor (a DuraAct™ patch transducer); however other piezoelectric material known in the art may be used. Also, different configuration of the piezoelectric material known in the art may be used. As a non-limiting example, the piezoelectric sensor used may consist of a single sheet to capture various temporal signals, or it can be formed as an array of small piezoelectric sensors to capture the temporal and spatial cardiac signals over the chest to give an added spatial granularity on top of the localized temporal signal. In FIG. 1, the output terminals of piezoelectric material 1 are connected to a digital oscilloscope 3. In some embodiments (not shown), the output terminals of the piezoelectric material may also be connected to a smart display through a microcontroller that can read the output voltage of the piezoelectric sensor.

In system 100, the periodic cardiac action of user 102 causes mechanical movement on the chest surface of user 102. Piezoelectric sensor 101, which is placed on the anterior chest surface of user 102, is then subjected to a mechanical load produced, at least, by the heart muscles contractions and expansions. The strain induced in piezoelectric sensor 101 generates a voltage. This energy conversion from the mechanical to the electrical is theoretically accounted for by a transformer with a turns ratio (not shown).

Figure 2:
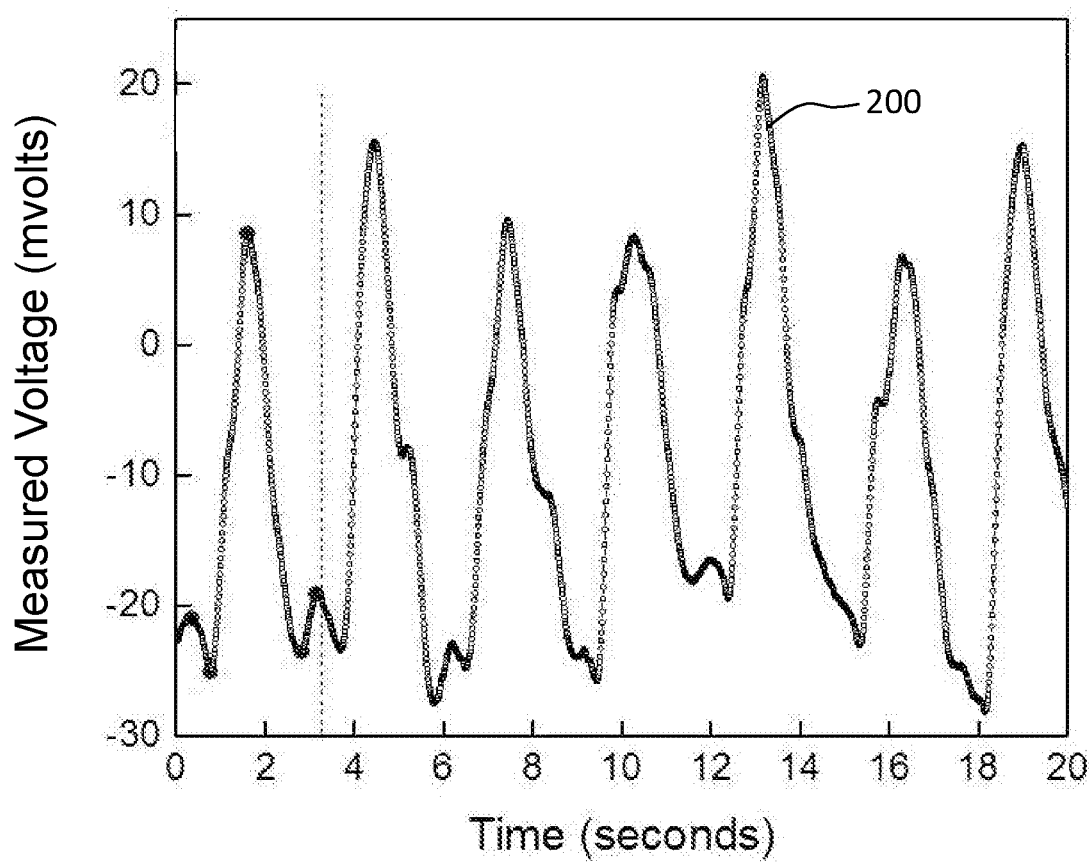
FIG. 2 shows an output voltage signal displayed on oscilloscope 3 in system 100 in FIG. 1.

The voltage signal generated by piezoelectric sensor 101 represents an instantaneous voltage output signal that may be displayed and recorded on oscilloscope 103. In some embodiments (not shown), the output terminals of the piezoelectric material may be connected to one or more smart displays through one or more microcontrollers that can read the output voltage of the piezoelectric sensor. FIG. 2 shows an output voltage signal 200 displayed on oscilloscope 103 in system 100 described above. As can be seen from FIG. 2, the measured open-circuit signal output is of a periodic nature and it repeats itself with little difference in shape every 3.75 seconds on average. The duration of a full cycle may vary from one subject to another, or even for the same subject, due to different parameters such age, gender, weight or other physiological and physical known parameters of a subject.

Signal 200 is a product of a multi-input, single output system, where the inputs may include, among others, cardiac parameters such as heartbeat and blood pressure. In some embodiments (not shown), the signal may also be a product of a multi-input, multi-output system. In order to extract the representation of cardiac parameters of interest from signal 200, piezoelectric theory and signal processing techniques are used.

As previously stated, induced stress in piezoelectric sensor 101 on the mechanical side is related to the output voltage produced in the sensors on the electrical side through the transformer. This induced stress is correlated with the real cardiac mechanical activity which is conformally mapped with the corresponding output voltage signal. The equivalent turns ratio for the transformer is given by:

$$n = -d_{31} c_p / t_c \quad (1)$$

where $c_p$ is the elastic constant for the piezoelectric material, $t_c$ is the piezoelectric beam thickness and $d_{31}$ is the piezoelectric voltage constant.

The relation between the stress acting on the piezoelectric transducers, represented by p(t), and output voltage signal, V(t), is given by:

$$p(t) = n*V(t) \quad (2)$$

where n is the piezoelectric turns ratio representing the mechanical to electrical conversion process in the transducer.

Signal processing algorithms are used to map and extract the corresponding set of cardiac signals. By way of non-limiting example, the different signals such as electrocardiogram (ECG) could be described using the convolution process, as follow:

$$ecg(t) = H(t)*p(t) \quad (3)$$

Where p(t) is the output voltage of the piezoelectric signal, ecg(t) corresponds to ECG time domain signal and H(t) is the time domain transfer function. It is to be understood that the same technique described herein may be used to extract other corresponding set of cardiac signals different from ECG. In addition the technique may also be used to extract signals specific to other physiological phenomena that may contribute to inducing mechanical stress on the piezoelectric material. By way of non-limiting example, the technique may be used to monitor breathing to check for parameters of interest in pulmonary related activities.

The transfer function H(t) could be found by simultaneously measuring the piezoelectric output as shown in Signal 200 in FIG. 2 and measuring the ECG signal with the conventional technique just for one time. This one time measurement of the ECG signal with conventional technique is for the purpose of mapping the electrical signal resulting from the mechanical cardiac activity, detected by the piezoelectric sensor, with a known accurate conventional measurement of the same activity.

Figure 3:
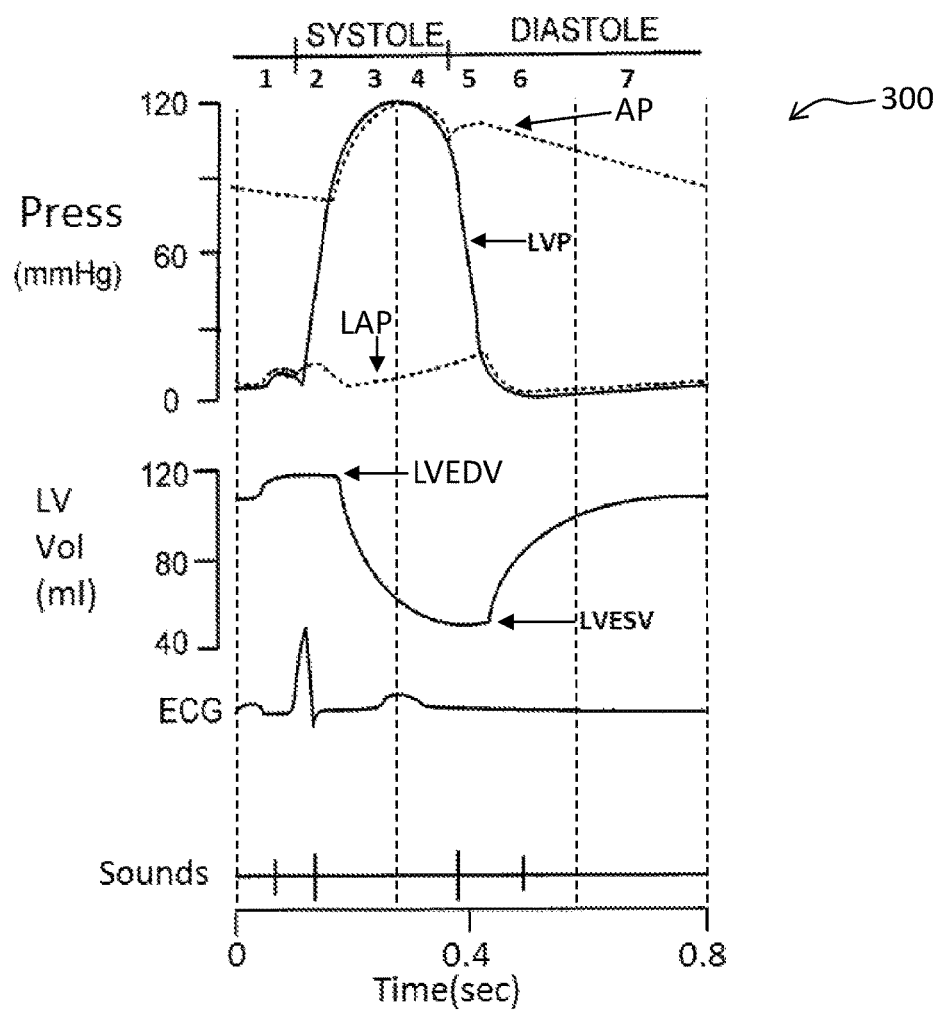
FIG. 3 shows a diagram which shows other cardiac cycle parameters including but not limited to Aortic Pressure (AP), Left Ventricle Pressure (LVP), Left Atrial Pressure (LAP), Left Ventricular Volume (LV Vol), and heart sounds, that could be found with the same manner during a single cycle of cardiac contraction and relation.

The one time measurement is to be understood to cover at least one full cycle of the cardiac activity but may also cover multiple cycles of the periodic cardiac activity, which may be averaged for more accuracy. For example, 10 or more cycles may be measured and averaged to allow for statistical accuracy. Given the periodic nature of the cardiac activity, a full cycle signal may best be identified as the signal falling between two peaks; alternatively, it can be generally identified between two points on a signal curve defining a full section which is periodically repeated in following section. In some embodiments, system 100 may utilise an adaptive algorithm to detect the beginning of a cycle in a piezoelectric generated signal (not shown). A cardiac cycle is well known in the art and it refers to a complete heartbeat from its generation to the beginning of the next beat, and so includes the diastole, the systole, and the intervening pause as shown in FIG. 3.

It should be noted that the conventional measurement is obtained for each subject the first time the system is used on such subject. Once the conventional measurement is conducted the first time, the data obtained for that subject is stored by the system and used for future reference, so that in later use of the system, conventional measurement of the same cardiac activity is not required, as long as the subject's physiological and physical characteristics are substantially unchanged. Such measurement may require updating if the subject experiences substantial physiological or physical changes, such as growth, aging, loss of weight or other physiological or physical changes known in the art that may affect the behaviour of the cardiac activity in the subject.

It is preferable that the conventional measurement of the signal and mapping with the electrical signal generated by the piezoelectric material be carried out when the subject is in good heart health condition so that the conventional measurement may be stored and used to determine later if there is some discrepancy. Moreover, if the subject has heart problems, then the typical constructed signal from the mechanical model can be used as a reference, by adjusting it to the corresponding parameters based, at least on, age, weight and gender. Other physiological or physical parameters and/or characteristics may be taken into consideration as well. Therefore, in that case, the system may be able to discriminate between sick and normal heart by the indicators status and also may be able to detect heart failure by prediction technique based on historical data that is stored by tracking up the indicators. Indicators are to be understood as the set of parameters that are extracted from the measured signal.

Moreover, in some cases, it may be preferable that measurements are done with the subject holding its breath. This will remove dependency of the piezoelectric generated electrical signal on mechanical movement related to the lungs and hence, the effect of respiratory cycle may be ignorable and excluded. The holding of the subject's breath may not be necessary for some types of subjects such as non-humans.

Referring back to equation (3), once P(t) and ECG(t) are obtain for the first initial use, a Fourier transform may be applied to the equation to result in:

$$ECG(f) = H(f)P(f) \qquad (4)$$

Where equation (4) is the frequency representation of equation (3). Upon manipulation of equation (4), H(f), which represents the frequency transfer function of the piezoelectric employed sensors, is represented as:

$$H(f) = \frac{ECG(f)}{P(f)} \qquad (5)$$

It should be noted that when the conventional measurement of ecg(t) is obtained for multiple cycles, averaging of the signal may be done before or after transforming the function into the frequency domain. Inverse Fourier transform may be applied to H(f) in order to obtain the transfer function H(t), which may then be introduced back into equation (3). Once that is done, the signal ecg(t) for any time may be found using equation (3), using the pre-determined transfer function H(t) and the piezoelectric generated electrical signal at that time, as presented in FIG. 2.

Alternatively, to construct the corresponding ECG signal at any time and directly from the measured output piezoelectric voltage, the following relationship may be used:

$$ecg'^{(t)} = F^{-1}\left[\left[\frac{ECG(f)}{P(F)}\right]P'(f)\right] \qquad (6)$$

Where $F^{-1}$ is the inverse Fourier transformation, P'(f) is the corresponding frequency domain of the measured piezoelectric output voltage and $$\left[\frac{ECG(f)}{P(F)}\right]$$

is found for only one time for each subject.

It is to be understood that the technique presented above may be applied to extract other cardiac activity parameter different than the heartbeat. FIG. 3 shows a diagram 300 which shows other cardiac cycle parameters including but not limited to Aortic Pressure (AP), Left Ventricle Pressure (LVP), Left Atrial Pressure (LAP), Left Ventricular Volume (LV Vol), which shows the left ventricular end diastolic volume (LVEDV) and the left ventricular end systolic volume (LVEDV), and heart sounds, that could be found with the same manner during a single cycle of cardiac contraction and relaxation.

Figure 4:
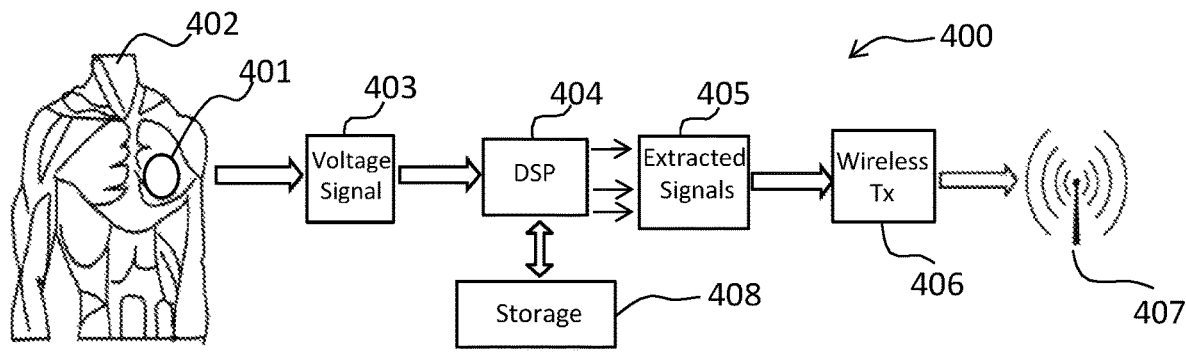
FIG. 4 shows a schematic representation of a cardiac monitory system 400 according to another embodiment of the invention.

In some embodiments, the system may include a processor and a memory storage device (404 and 408, respectively in FIG. 4). The processor and memory device may be provided in a same device or in separate devices. FIG. 4 shows the processor and the storage device separate. The processor may apply an adaptive algorithm to detect the beginning of a cycle in the piezoelectric generated electrical signal and to average the cycles once a full cycle is identified. The processor may then map the piezoelectric generated signal with the conventionally measured signal of the specific cardiac activity, where such conventional signal may be stored on the memory storage device for later reference. The transfer function H(t) may also be stored on the memory storage device for later access by the processor.

When the system is used by the same subject at a later time, the processor accesses the transfer function H(t) from the memory storage device and uses it to extract from the new piezoelectric generated electric signal a signal representative of a specific cardiac parameter, which corresponds to the transfer function H(t). The processor may then access the conventional signal previously stored for the same subject and compare it to a new generated representative signal using auto-correlative correlation. If the result of the correlation is found to be high, the processor may then yield a notification indicative of a good result or a bad result to the user if the correlation is found to be high or low, respectively. In some embodiments (not shown), pre-determined values are set as threshold on which assessment values are compared and based on the comparison, an evaluation of a good or a bad correlation is provided by the processor. Such pre-determined values may vary from one subject to another and may be based on gender, age, weight and other philological and/or physical characteristics known in the art.

The memory storage device may also include at least one pull-up library of conventional measurements for signals representing known cardiac defects for different individuals. Such signals may include marker regions and may be classified in the pull-up library by age, gender, weight, or other physiological and/or physical characteristics. When the system is used by the same subject described above, in addition to the process described above, the processor may also access some of the stored signals in the pull-up library, based on physiological and physical characteristics initially provided about the subject, and performs a cross correlation comparison between each one of the signals selected from the pull-up library and the piezoelectric representative signal generated for a specific cardiac parameter for the subject. If the result of the correlation is found to be higher than a pre-determined value around the region representing the cardiac defect, the processor may then yield a notification indicative of a possible diagnosis of the cardiac disease. If the result of the correlation is found to be lower than a pre-determined value around the region representing the cardiac defect, the processor may then yield a notification indicative of a normal reading or a notification indicative of the tested disease and the lack of presence of indicators of concern relating to that indicator. Different notification, alerting and warning techniques known in the art may be used to convey the output of the system.

In the embodiment described above, the system may also include a wired or wireless transmitter (not shown). The processor may communicate, using the transmitter, a message or a notification to the subject being examined and/or to a third party based on the results obtained. By way of non-limiting example, the message may provide that the subject is in need of a check-up by a physician. The message may include the signal generated in a format familiar to the physician so that it may be used directly for making a diagnosis. If the subject is in distress, the message may be communicated to an emergency unit to provide the subject with some emergency care. The message may also include information about the subject as well as the location of such individual.

FIG. 4 shows a schematic representation of a cardiac monitoring system 400 according to another embodiment of the invention. In system 400, electrical signal 403 is generated by piezoelectric sensors 401 located on or near the chest of user 402. Signal 403 is then manipulated using digital signal processing and piezoelectric theory, shown to occur in processor 404 in FIG. 4, as described above, to extract signals relating to particular cardiac parameters, which is shown as 405 in FIG. 4. System 400 further provides a transmitter 406, which is used to transmit the extracted signals wirelessly in accordance with any known wireless transmission techniques known in the art. The transmitted signal is then received by a receiver, shown in FIG. 4 as 407. The receiver may be in proximity to the subject and the processing of the signal once received may also be done in proximity of the subject.

Figure 5:
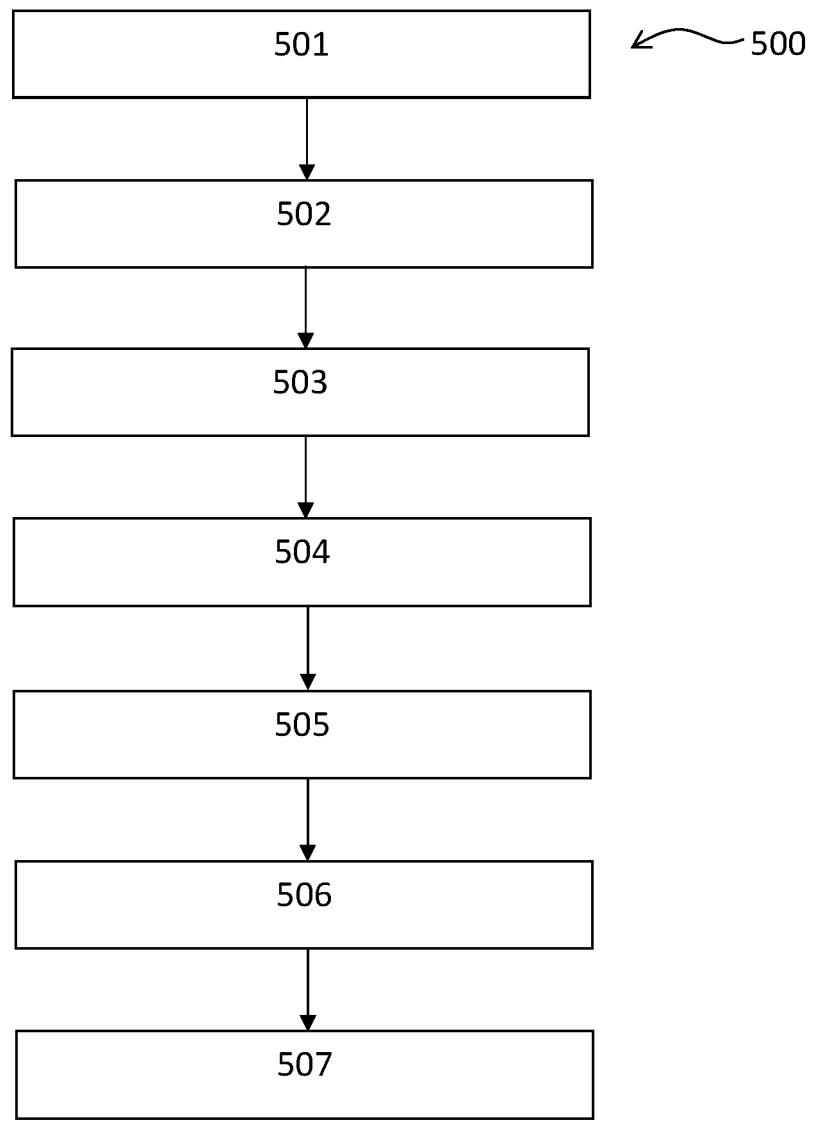
FIG. 5 shows a schematic block diagram representing a method according to an embodiment of the invention.

In some embodiments, the signal processing may be performed away from the subject. In such embodiments (not shown), piezoelectric sensors may be attached to the subject and a transmitter may be either attached to the subject or may be carried by the subject. The transmitter may be located at a distance away from the sensor to reduce noise and/or interference. FIG. 5 shows a schematic block diagram representing the method 500 implemented in such embodiment. In method 500, step 501 describes an array of piezoelectric sensors generating an electrical signal based on the mechanical movement of the chest of the subject, to which the sensors are attached. Step 502 describes passing the signal by a processor to a first conditional circuit for amplification. Step 502 may be skipped if the signal is determined to be above a pre-determined threshold, which is determined based, at least, on the type of the processor and transmitter, and the processor may transmit the signal directly without amplification according to step 503. The pre-determined threshold value may also be dependent on additional parameters such as age, gender, weight and other physiological and/or physical parameters. Once transmitted, step 504 shows the signal being received by a receiver system. Once received, step 505 shows the signal being passed by a second conditioning circuit for amplification. Step 505 may also be skipped if the received signal is determined to be above a pre-determined threshold. The pre-determined threshold conditions may be the same as or different from the ones identified in step 502. The signal is then processed by a signal processing unit at step 506. The receiver and the processor may be at the same location or a location different than the location of the transmitter. At step 507, the processing unit is used to extract signals representative of cardiac parameters of interest, according to the method described above. The extracted signals are then assessed remotely according to the method described above.

In application, method 500 allows for the possibility of continuous monitoring of cardiac activity using a passive, compatible and compact contactless probing system with the ability to model the human chest impulsive response incorporating the cardiac cycle parameters. The same objective may be achieved when used on other living organisms with a beating heart or organ. This may be achieved because of the light weight characteristic of the piezoelectric material, the wide range of cardiac cycle parameters that may be broadcasted from the transmitter, the receiver system and the ability to remotely process the signal once received.

In the description above, it is provided that the piezoelectric sensors are positioned in areas on the chest close to the organ producing the cardiac mechanical movement, i.e. the heart. This is because the chest is understood to act as a bulky chest membrane that dampens the mechanical movement. Therefore, the closer the piezoelectric sensors are placed to the source of the mechanical movement, the stronger the mechanical movement detected and therefore, the stronger the electrical signal generated. However, with use of amplifiers and signal-to-noise enhancement techniques known in the art, it may be possible to position the piezoelectric sensors on a part of the subject's body different than the chest area and still be able to achieve a compatible and compact contactless probing system with the ability to model the impulsive response incorporating the cardiac cycle parameters.

Interpretation of Terms

Unless the context clearly requires otherwise, throughout the description and the claims:

- "comprise," "comprising," and the like are to be construed in an inclusive sense, as opposed to an exclusive or exhaustive sense; that is to say, in the sense of "including, but not limited to".
- "connected," "coupled," or any variant thereof, means any connection or coupling, either direct or indirect, between two or more elements; the coupling or connection between the elements can be physical, logical, or a combination thereof.
- "herein," "above," "below," and words of similar import, when used to describe this specification shall refer to this specification as a whole and not to any particular portions of this specification.

"or," in reference to a list of two or more items, covers all of the following interpretations of the word: any of the items in the list, all of the items in the list, and any combination of the items in the list.

the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

Where a component (e.g. a circuit, module, assembly, device, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions and sub-combinations as may reasonably be inferred. The scope of the claims should not be limited by the preferred embodiments set forth in the examples, but should be given the broadest interpretation consistent with the description as a whole.

What is claimed is:

1. A method of using piezoelectric material to monitor a physiological activity of a subject and generate a physiological electrical signal corresponding to a physiological parameter the method comprising:
   coupling the piezoelectric material to a body part of the subject;
   obtaining a first piezoelectric electrical signal from the piezoelectric material, the first piezoelectric electrical signal is based on mechanical movement of the body part, the mechanical movement related to the physiological activity of the subject;
   mapping a segment of the first piezoelectric electrical signal to a conventional electrical signal obtained using conventional techniques for the physiological parameter of the subject, the conventional electrical signal is obtained only once and is obtained simultaneously while obtaining the segment of the first piezoelectric electrical signal, the segment of the first piezoelectric electrical signal and the conventional electrical signal are obtained for at least one full cycle of activity for the physiological parameter, the mapping is performed using signal processing techniques; the signal processing techniques comprise generating a transfer function representative of the physiological parameter; and
   generating solely from a subsequent segment of the first piezoelectric electrical signal a first physiological electrical signal corresponding to the physiological parameter based on the transfer function.

2. A method according to claim 1, where the mapping of the first piezoelectric electric signal to the conventional electrical signal is performed using a linear one-to-one mapping.

3. A method according to claim 1, the method further comprising storing the transfer function on a memory storage device.

4. A method according to claim 3, the method further comprising: storing in the memory storage device a plurality of conventional electrical signals obtained from the conventional techniques, wherein each of the plurality of conventional electrical signals corresponds to a different known physiological defect of the physiological parameter.

5. A method according to claim 4, wherein the method further comprises:
   comparing the first physiological electrical signal to each of the plurality of conventional electrical signals; and
   assessing whether the subject has a physiological defect of the physiological parameter based on the comparison.

6. A method according to claim 1, the method further comprising:
   obtaining a second piezoelectric electrical signal different from the first piezoelectric electrical signal, the second piezoelectric electrical signal based on a second mechanical movement of the body part at a time after obtaining the first piezoelectric electrical signal, the second mechanical movement related to the physiological activity of the subject;
   manipulating the second piezoelectric electrical signal by convolving the second piezoelectric electrical signal with the transfer function; and
   generating solely from the manipulated second piezoelectric electrical signal a second physiological electrical signal corresponding to the physiological parameter.

7. A method according to claim 6, the method further comprising:
   comparing the first physiological electrical signal with the second physiological electrical signal; and assessing a health condition of the subject based on the comparison.

8. A method according to claim 6, the method further comprising:
   comparing the first physiological electrical signal and the second physiological electrical signal; and
   assessing the subject to have a positive condition or a negative condition based on the comparison.

9. A method according to claim 8, wherein the subject is assessed to have the positive condition if the second physiological electrical signal and the first physiological electrical signal have a correlation value higher than a pre-determined value; and
   wherein the subject is assessed to have the negative condition when the second physiological electrical signal and the first physiological electrical signal have a correlation value lower than the pre-determined value.

10. A method according to claim 9, the method further comprising: notifying the subject of the positive or negative condition.

11. A method according to claim 9, the method further comprising notifying a third party of the positive or negative conditions.

12. A method according to claim 1, wherein obtaining the first piezoelectric electrical signal and the conventional electrical signal is performed when the subject is in good health condition.

13. A method according to claim 1, wherein the physiological activity is cardiac activity, the physiological parameter is a cardiac parameter and wherein the subject performs a breath hold while the first piezoelectric electrical signal and the conventional electrical signal are obtained.

14. A method according to claim 13, wherein the cardiac parameter is one of Aortic Pressure AP, Left Ventricle Pressure LVP, Left Atrial Pressure LAP, Left Ventricular Volume LV Vol, and heart sounds.

15. A method according to claim 1, wherein the method further comprises:
    wirelessly transmitting the first piezoelectric electrical signal using a transmitter; and
    receiving the transmitted first piezoelectric electrical signal using a receiver located at a location away from the transmitter,
    wherein the generating solely from the subsequent segment of the first piezoelectric electrical signal the first physiological electrical signal corresponding to the physiological parameter based on the transfer function is performed at the location of the receiver.

16. A method according to claim 15, wherein the method further comprises:
    comparing the first piezoelectric electrical signal to a pre-determined threshold before transmitting the first piezoelectric electrical signal by the transmitter and amplifying the first piezoelectric electrical signal before transmitting the first piezoelectric electrical signal if the first piezoelectric electrical signal is determined to be below the pre-determined threshold; and
    comparing the first piezoelectric electrical signal after receiving the first piezoelectric electrical signal by the receiver and amplifying the first piezoelectric electrical signal after receiving the first piezoelectric electrical signal by the receiver if the first piezoelectric electrical signal is determined to be below the pre-determined threshold.

17. A method according to claim 1, wherein the physiological activity is periodic and the monitoring of the physiological activity is performed continuously and wherein the method further comprises:
    obtaining additional piezoelectric electrical signals different from the first piezoelectric electrical signal, the additional piezoelectric electrical signals are obtained individually and sequentially after the first piezoelectric electrical signal, the additional piezoelectric electrical signals are based on additional mechanical movement of the body part related to the physiological activity of the subject;
    manipulating each of the additional piezoelectric electrical signals by convolving each of the additional piezoelectric electrical signals with the transfer function;
    generating solely from each of the manipulated additional piezoelectric electrical signals an additional physiological electrical signal corresponding to the physiological parameter;
    comparing the first physiological electrical signal and the additional physiological electrical signal for each of the manipulated additional piezoelectric electrical signals; and
    continuously assessing a health condition of the subject based on the comparison.

18. A method according to claim 17, the method further comprises notifying at least one of the subject and a third party of the health condition of the subject.

19. A system for monitoring a physiological activity of a subject and generating a physiological electrical signal corresponding to a physiological parameter using piezoelectric material, the system comprising:
    at least one piezoelectric sensor couplable to a body part of the subject; the at least one piezoelectric sensor for obtaining a first piezoelectric electrical signal using the piezoelectric material, the first piezoelectric electrical signal is based on mechanical movement of the body part, the mechanical movement related to the physiological activity of the subject; and
    a processor in electrical communication with the at least one piezoelectric sensor, the processor configured to:
        receive the first piezoelectric electrical signal from the at least one piezoelectric sensor;
        use signal processing techniques to map a segment of the first piezoelectric electrical signal to a conventional electrical signal obtained using conventional techniques for the physiological parameter of the subject, the conventional electrical signal is obtained only once and is obtained simultaneously while obtaining the segment of the first piezoelectric electrical signal, the segment of the first piezoelectric electrical signal and the conventional electrical signal are obtained for at least one full cycle of activity for the physiological parameter, the signal processing techniques comprise generating a transfer function representative of the physiological parameter; and
        generate solely from a subsequent segment of the first piezoelectric electrical signal a first physiological electrical signal corresponding to the physiological parameter based on the generated transfer function.

* * * * *